(12) United States Patent
Braun et al.

(10) Patent No.: US 8,440,865 B2
(45) Date of Patent: *May 14, 2013

(54) PROCESS FOR THE MANUFACTURE OF ALKENONES

(75) Inventors: Max Braun, Wedemark (DE); Stefan Palsherm, Barsinghausen (DE); Uta Claassen, Hohenhameln (DE); Alain Lambert, Beauvechain (BE)

(73) Assignee: SOLVAY SA, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/999,750

(22) PCT Filed: Jul. 5, 2010

(86) PCT No.: PCT/EP2010/059556
§ 371 (c)(1),
(2), (4) Date: Apr. 7, 2011

(87) PCT Pub. No.: WO2011/003860
PCT Pub. Date: Jan. 13, 2011

(65) Prior Publication Data
US 2012/0116127 A1    May 10, 2012

Related U.S. Application Data

(63) Continuation-in-part of application No. PCT/EP2009/058525, filed on Jul. 6, 2009.

(30) Foreign Application Priority Data

Jan. 7, 2010    (EP) .................................... 10150276

(51) Int. Cl.
C07C 45/64    (2006.01)

(52) U.S. Cl.
USPC ............................................. 568/392; 568/404

(58) Field of Classification Search ................ 568/392, 568/404
See application file for complete search history.

(56) References Cited

U.S. PATENT DOCUMENTS

| 5,708,175 A | 1/1998 | Koyanagi et al. |
| 7,057,079 B2 | 6/2006 | Braun et al. |
| 2006/0084813 A1 | 4/2006 | Hausmann et al. |

FOREIGN PATENT DOCUMENTS

| WO | WO 03066558 A2 | 8/2003 |
| WO | WO 20040108647 A2 | 12/2004 |
| WO | WO 20100000871 A2 | 1/2010 |
| WO | WO 20100037688 A1 | 4/2010 |
| WO | WO 20110003854 A1 | 1/2011 |
| WO | WO 20110003856 A1 | 1/2011 |

OTHER PUBLICATIONS

Tietze, L. F., et al—"Synthesis of Alkyl Propanoates by a Haloform Reaction of a Trichloro Ketone: Preparation of ethyl 3,3-Diethoxypropanoate"; Organic Syntheses, 1990, vol. 69, pp. 238-244, XP 008037891; 7 pgs.
U.S. Appl. No. 12/999,673, filed Dec. 17, 2010, Max Braun, et al.
U.S. Appl. No. 13/120,505, filed Mar. 23, 2011, Max Braun.
U.S. Appl. No. 12/999,714, filed Mar. 31, 2011, Max Braun, et al.
U.S. Appl. No. 12/999,730, filed May 23, 2011, Max Braun, et al.

*Primary Examiner* — Sikarl Witherspoon
(74) *Attorney, Agent, or Firm* — Beatrice C. Ortego

(57) ABSTRACT

Process for preparing an alkenone, which comprises the following steps: (a) providing a halogenated precursor of the alkenone; and (b) eliminating the hydrogen halide from said precursor to form the alkenone by a thermolysis treatment selected from the group consisting of flash thermolysis, vacuum thermolysis, and thermolysis under stripping with inert gas.

19 Claims, No Drawings

PROCESS FOR THE MANUFACTURE OF ALKENONES

CROSS-REFERENCE TO RELATED APPLICATIONS

This application is a U.S. national stage application under 35 U.S.C. §371 of International Application No. PCT/EP2010/059556 filed on Jul. 5, 2010, which claims priority under 35 U.S.C. §119(a)-(d) or (f), §365(b) or §365(a) to International Application No. PCT/EP2009/058525 filed on Jul. 6, 2009 and to European Application No. EP-10150276.3 filed on Jan. 7, 2010, said International Application PCT/EP2010/059556 being a continuation-in-part application under 35 U.S.C. §365(c) of International Application No. PCT/EP2009/058525 designating the United States and filed on Jul. 6, 2009, the whole content of each of these applications being incorporated herein by reference for all purposes.

The present invention relates to a process for preparing alkenones.

Halogenated alkenones, such as 4-ethoxy-1,1,1-trifluoro-3-butenone (ETFBO), are building blocks in chemical synthesis, as disclosed, for example, in U.S. Pat. No. 5,708,175. They may be prepared by reacting an acid chloride with a vinyl ether in the presence of a base, as described in the aforementioned U.S. patent. For this reaction, the base may also be used in excess as a solvent.

WO 03/066558 discloses production of alkenones from vinyl ethers and acid halides or acid anhydrides in the presence of onium salts.

US 2006084813 A1 discloses i.a. simplified production of alkenones comprising addition of carboxylic acid halides to vinyl ethers. The reference discloses that the addition product may be thermolyzed at temperatures up to 150° C. The production of alkenones may be carried out at ambient pressure or under slight vacuum. Generated hydrogen halide may be removed from the reaction mixture during or after the reaction e.g. by heating, vacuum or both.

The present invention now makes available an improved process for the preparation of alkenones, in particular concerning the selectivity and the yield of the production, whereby, amongst others, separation of the product can be simplified and loss of material and need for disposal of by-products can be reduced.

The invention relates to a process for preparing an alkenone, which comprises the following steps:
(a) providing a halogenated precursor of the alkenone, preferably by manufacture from a carboxylic acid halide and a vinyl ether in accordance with any of the processes disclosed herein before or a combination thereof
(b) eliminating the hydrogen halide from said precursor to form the alkenone by a thermolysis treatment selected from a flash thermolysis, a vacuum thermolysis and a thermolysis under stripping with an inert gas.

More particularly, the invention relates to a process for preparing an alkenone, which comprises the following steps:
(a) providing a halogenated precursor of the alkenone
(b) eliminating the hydrogen halide from said precursor to form the alkenone by a thermolysis treatment selected from a thermolysis carried out at a temperature from greater than 90° C. to 120° C., a flash thermolysis, vacuum thermolysis carried out at a temperature from 60° C. to 140° C. and thermolysis under stripping with inert gas.

It has been found, surprisingly, that the process according to the invention, in particular a flash thermolysis, allows for high conversion of the halogenated precursor of the alkenone, under productive conditions. The process according to the invention also allows for particularly high selectivity, including configuration isomer selectivity, to alkenone, in particular ETFBO. The high selectivity allows further for simplified purification and high isolated yield of the target product.

In step b), 2 or more thermolysis treatments can be combined. For example, thermolysis can be carried out at a temperature from greater than 90° C. to 120° C. under stripping with inert gas, or a vacuum thermolysis is combined with stripping with inert gas.

The process according to the invention can advantageously be applied to preparation of an alkenone corresponding to Formula (I): R1-C(O)—C(H)=C(H)—OR2 (I) wherein R1 represents a C1-C10 alkyl group which is optionally substituted by at least one halogen atom or R1 represents CF3, CF2Cl, CF2H; and R2 represents aryl, substituted aryl, or a C1-C10 alkyl group which is optionally substituted by at least one halogen atom wherein an acid halide corresponding to Formula (II): R1-C(O)X (II) in which X represents fluorine, chlorine or bromine and R1 has the meaning given above, is reacted with a vinyl ether corresponding to Formula (III): CH2=C(H)—OR2 (III) in which R2 has the meaning given above.

R1 is often a fluorinated C1-C4 alkyl group. R1 preferably represents methyl, ethyl, n-propyl, isopropyl or methyl, ethyl, n-propyl or isopropyl substituted by at least one fluorine atom. It is especially preferred if R1 represents methyl, ethyl or methyl or ethyl substituted by at least one fluorine atom. CF3, CF2H, CF2Cl, C2F5, C3F7 are particularly preferred as R1. CF3, CF2Cl and CF2H are more particularly preferred as R1.

R2 can be selected for example from aryl, for example, phenyl, C1-C4 alkyl groups and/or phenyl substituted by halogen atoms. R2 is often a C1-C4 alkyl group. Preferably, R2 represents a linear or branched C1-C4 alkyl group, and particularly preferably R2 represents methyl, ethyl, n-propyl or isopropyl, most preferably a methyl or an ethyl group.

X is preferably selected from fluorine and chlorine, more preferably X is chlorine.

In a first particular embodiment, the carboxylic acid halide is trifluoroacetyl chloride.

In a second particular embodiment, the carboxylic acid halide is Chlorodifluoroacetyl chloride.

In a third particular embodiment, the carboxylic acid halide is Difluoroacetyl chloride.

In a forth particular embodiment, the carboxylic acid halide is trifluoroacetyl fluoride.

In a fifth particular embodiment, the carboxylic acid halide is (trifluoroaceto)acetyl fluoride.

Step (a) of the process according to the invention comprises providing a halogenated precursor of the alkenone. This can be carried out for example by filling or pumping halogenated precursor to a reaction zone wherein step (b) is carried out. The halogenated precursor may be supplied for example by transportation of previously produced halogenated precursor in a suitable tank. However, it is preferably provided by reaction of precursors thereof.

Suitable embodiments in particular for manufacture of 4-chloro-4-ethoxy-1,1,1-trifluoro-butane-3-one (CETFBO) from ethyl vinylether (EVE) and trifluoroacetylchloride (TFAC) are selected from (a) carrying out the reaction in a reaction medium containing carboxylic acid halide, (b) carrying out the reaction in a reaction medium using alkenone and/or halogenated precursor as solvent, (c) carrying out the reaction under conditions allowing to avoid or minimize hot spots, in particular by carrying out the reaction in a turbulent state, (d) carrying out the reaction in the absence of an acid scavenger for hydrogen halide and combinations of these embodiments. These embodiments are explained in further detail in US 2006084813, PCT/EP/2009/058525 and co-pending European Appl. No. 10150234.2 and 10150229.2, the contents of which is incorporated by reference into the present patent application.

In a preferred embodiment of the present invention, the process for preparing an alkenone comprises the following steps:

(a) providing a halogenated precursor of the alkenone wherein at least two of the following features are performed: (1) carrying out the reaction in a reaction medium containing carboxylic acid halide, (2) carrying out the reaction in a reaction medium using alkenone and/or halogenated precursor as solvent, (3) carrying out the reaction under conditions allowing to avoid or minimize hot spots, in particular by carrying out the reaction in a turbulent state, (4) carrying out the reaction in the absence of an acid scavenger for hydrogen halide (b) eliminating the hydrogen halide from said precursor to form the alkenone by a thermolysis treatment selected from a thermolysis carried out at a temperature from greater than 90° C. to 120° C., a flash thermolysis, vacuum thermolysis carried out at a temperature from 60° C. to 140° C. and thermolysis under stripping with inert gas.

In an especially preferred embodiment, the process for preparing an alkenone comprises the following steps:

(a) providing a halogenated precursor of the alkenone wherein the reaction is carried out in a reaction medium containing carboxylic acid halide, and the reaction is carried out in a reaction medium using alkenone and/or halogenated precursor as solvent, and the reaction is carried out under conditions allowing to avoid or minimize hot spots, in particular by carrying out the reaction in a turbulent state, and the reaction is carried out in the absence of an acid scavenger for hydrogen halide (b) eliminating the hydrogen halide from said precursor to form the alkenone by a thermolysis treatment selected from a thermolysis carried out at a temperature from greater than 90° C. to 120° C., a flash thermolysis, vacuum thermolysis carried out at a temperature from 60° C. to 140° C. and thermolysis under stripping with inert gas.

In one embodiment of the process according to the invention and the particular embodiments thereof which is advantageous when the process is carried out batch-wise, steps (a) and (b) are carried out in the same reaction zone, for example, a vessel surmounted by a distillation column.

In another, preferred, embodiment of the process according to the invention and the particular embodiments thereof, which is advantageous when the process is carried out continuously, step (a) is carried out in a first reaction zone and step (b) is carried out in a second reaction zone different from the first reaction zone.

The first reaction zone is often an optionally stirred tank reactor preferably a continuously stirred tank reactor. The second reaction zone can be, for example, a distillation column.

Thermolysis in the sense of the present invention can suitably be carried out by heating a liquid fraction comprising halogenated precursor to the temperature of the thermolysis treatment. Heating can be carried out by suitable means such as in particular contacting the liquid fraction with a heated solid body such as for example, the walls of a reactor, a heat exchanger and a heated pipe. Heating can also be carried out by providing a hot gas, in particular a hot inert gas such as in particular nitrogen to the liquid fraction.

The thermolysis in the process according to the invention is suitably carried out in an apparatus facilitating withdrawal of formed gaseous hydrogen halide from the liquid fraction. Often, such apparatus include means for increasing the surface of the liquid fraction. "Means for increasing the surface of the liquid fraction" is understood to denote in particular any means which provides an increased surface of the liquid fraction in contact with a gas phase when compared with the surface which is in contact with a gas phase of the same volume of liquid fraction when filled into a spherical flask having double volume of the liquid phase. Particular examples of such apparatus include film evaporators and, preferably columns having a flow resistance. Use may be made, for example, of plate columns or plate columns of dual-flow type or preferably of columns with bulk or structured packing. Particular examples of suitable columns are packed, for example with Pall or preferably Raschig rings.

The means for increasing the surface of the liquid fraction is generally connected to at least one line allowing for withdrawal of a gas stream, in particular a hydrogen halide stream. If desired such line may also be used to apply a vacuum, in particular as described herein. The means for increasing the surface of the liquid fraction may be connected, if desired, to at least one line allowing for supply of inert gas in particular as described herein.

When a means for increasing the surface of the liquid fraction is used, heating of the liquid fraction may be suitably provided externally, for example by circulating the liquid fraction between the means for increasing the surface of the liquid fraction and a means for heating, in particular as described above, preferably a heat exchanger.

The temperature of the thermolysis treatment is often at least 50° C., often equal to or greater than 60° C., preferably equal to or greater than 70° C. preferably equal to or greater than about 80° C. The temperature of the thermolysis treatment is generally less than 150° C., often less than 140° C., preferably less than or equal to 130° C. A thermolysis treatment carried out at a temperature from 90° C. to 120° C., in particular about 100° C. is particularly preferred. It has been found that this temperature range is particularly efficient, in particular for thermolysis of CETFBO to ETFBO.

For the purpose of the present invention, the term "flash thermolysis" refers to a process wherein the liquid reaction medium is heated up in a short time. Typical heating times for flash thermolysis are less than 1 hour, in particular less than 30 min, preferably about 15 minutes. Generally, the heating time is greater than 1 s, often greater than 15 s.

"Heating time" is understood to denote in particular the time required to heat the liquid fraction containing halogenated precursor, in particular a liquid reaction medium, from an initial temperature to the temperature of the thermolysis treatment. A typical initial temperature is less than 50° C., often less than 40° C., preferably equal to or less than 30° C. In one aspect, the temperature is preferably equal to or less than about −25° C. The initial temperature is generally at least −50° C., often equal to or greater than −40° C., preferably equal to or greater than −30° C. Often, the initial temperature corresponds to the temperature with which the alkenone precursor leaves its manufacturing process.

In an stirred tank reactor, for example, the reaction temperature for the addition of the acid halide to a vinyl ether is often carried out at a temperature from 0° C. to 40° C. Consequently, the initial temperature of the precursor is also in that range.

In particular aspects of the process according to this embodiment, the flash thermolysis is conducted at a temperature ranging from −20° C. to 140° C. and a period of time ranging from 30 seconds to 1 hour, preferably at a temperature ranging from 0° C. to 130° C. and a period of time ranging from 30 seconds to 30 min, more preferably at a temperature ranging from 20° C. to 120° C., preferably from 50° C. to 120° C. and a period of time ranging from 30 seconds to 20 min.

An additional advantage of the flash thermolysis is that the formation of the Hetero-Diels-Alder product of 2 molecules of the alkenone, especially when ETFBO is prepared, is avoided. The Hetero-Diels-Alder product is increasingly formed if the thermolysis is performed in a too long time range.

The thermolysis or flash thermolysis, in particular as described herein before, can be optionally carried out under stripping with an inert gas stream such as nitrogen gas, argon gas.

For the purpose of the present invention, the term "stripping" denotes in particular a physical separation process where one or more components, in particular HCl, are removed from the liquid reaction medium by a gas stream. The liquid and gas streams can have concurrent or countercurrent flow directions.

If appropriate, the stripping is advantageously carried out with a nitrogen stream.

The process according to this embodiment, generally comprises carrying out the thermolysis at a temperature of −20° C. to 140° C., preferably from 60 to 130° C., for example at equal to or about 80° C. and more preferably at equal to or about 120° C.

The thermolysis or flash thermolysis may be carried out under vacuum. In that case, the vacuum is often from 100 to 600 mbar, preferably from 100 mbar to lower than 500 mbar, for example from 200 to 450 mbar.

It is understood that the different processes and embodiments disclosed herein apply in most preferred way to the manufacture of halotrifluoroalkoxybutanones, especially chlorotrifluoroalkoxybutanone from alkyl-vinylether and trifluoroacetic acid halide, in particular from trifluoroacetyl chloride and ethyl vinyl ether and subsequent elimination to form trifluoroalkoxybutenone, in particular ETFBO.

It is understood that the different processes and embodiments disclosed herein apply in most preferred way to the manufacture of halodifluoroalkoxybutanones, especially chlorodifluoroalkoxybutanone from alkyl-vinylether and difluoroacetic acid halide, in particular from difluoroacetyl chloride and ethyl vinyl ether and subsequent elimination to form difluoroalkoxybutenone, in particular 4-ethoxy-1,1-difluoro-3-butenone (EDFBO).

The examples here after are intended to illustrate the invention without however limiting it.

In these examples and throughout this specification the abbreviations employed are defined as follows: TFAC is trifluoroacetylchloride, EVE is ethyl vinyl ether, CETFBO is 4-Chloro-4-Ethoxy-1,1,1-trifluoro-3-butan-2-one, ETFBO is Ethoxy-1,1,1-trifluoro-3-buten-2-one.

EXAMPLE

Two-step manufacture of
4-Ethoxy-1,1,1-trifluoro-3-buten-2-one

Step (a)

In a 100 ml three-necked flask surmounted by a dry-ice cooler, equipped with a Pt100 internal thermometer 66.24 g (0.5 mole) trifluoroacetylchloride was condensed in at −30° C. 36.06 g (0.5 mole) of ethyl vinyl ether was added dropwise over 1 hour. After the addition, further 0.5 mole trifluoroacetylchloride was added. GC of a sample showed almost quantitative yield of 4-Chloro-4-Ethoxy-1,1,1-trifluoro-3-butan-2-one.

Step (b)

After the reaction of step (a) described above, the flask was warmed to room temperature and subjected to fractional distillation in vacuo. A first fraction (B.P. 59.3-66.4° C. at 47 mbar) contained a mixture of 4-Chloro-4-Ethoxy-1,1,1-trifluoro-3-butan-2-one and 4-Ethoxy-1,1,1-trifluoro-3-buten-2-one, which could be redistilled to provide further 4-Ethoxy-1,1,1-trifluoro-3-buten-2-one. A second fraction (B.P. 66.4-70° C. at 30 mbar) contained pure Ethoxy-1,1,1-trifluoro-3-buten-2-one (E/Z ratio 98.5:1.5). The isolated yield was 97.5% of theoretical yield.

EXAMPLE 2

Manufacture of 4-Chloro-4-Ethoxy-1,1,1-trifluoro-3-butan-2-one and 4-Ethoxy-1,1,1-trifluoro-3-buten-2-one under turbulent conditions and ETFBO as solvent.

General procedure: Pure ETFBO, obtained by a previous synthesis, was placed into the flow part of a recirculation system and cooled using a chiller. This recirculation system comprises a 20 L flask, 2 one meter distillation columns filled with 10 mm glass Raschig rings placed on top of another distillation column, a circulation pump (1500l/h), 3 tube reactors each with 3 m path length (diameter 1.5 cm). Once the desired temperature was reached in the recirculation system, gaseous or liquid trifluoroacetylchloride (15 kg/h; 113.2 mol/h) was introduced in the turbulent circulation in front of the first 3 m reactor and then a small molar excess of ethyl vinyl ether (TFAC/EVE=1:1.01) was added after the first 3 m reactor. The level in the 20 L flask of the recycle apparatus was kept constant by pumping material using a membrane pump into a second apparatus. This second apparatus which served for the thermolysis of 4-Chloro-4-Ethoxy-1,1,1-trifluoro-3-butan-2-one (CETFBO) to 4-Ethoxy-1,1,1-trifluoro-3-buten-2-one (ETFBO), comprised a 100 L Pfaudler ceramic vessel with 3 one meter distillation columns filled with 10 mm glass Raschig rings and a cooler with removal. The conversion of CETFBO to ETFBO under loss of HCl took place either through batchwise thermolysis when the ceramic vessel is full or through continuous feeding of the CETFBO stream from the recycle apparatus. The fine distillation was further carried out continuously or batchwise in the distillation columns.

EXAMPLE 2a

The recirculation system was filled with pure ETFBO and cooled to a temperature of 10° C. Following the general procedure, TFAC and EVE were introduced at a rate of 12.4 mol/h and 12.8 mol/h, respectively. A GC sample taken every hour at the top of the recycle apparatus, showed a complete reaction from TFAC with EVE whereby the CETFBO concentration was increasing continuously with a decreasing of the ETFBO concentration. The continuous introduction of TFAC and EVE was carried out during 8 hours and all the material was collected in the ceramic vessel. The thermolysis was carried out at 80° C. under a nitrogen stream, followed by a fractional distillation to provide 4-Ethoxy-1,1,1-trifluoro-3-buten-2-one in an isolated yield of 87% of the theoretical yield and with a purity (cis+trans isomer) of 98%.

EXAMPLE 2b

The same procedure was followed as example 2a but the recirculation system was kept at a temperature of 20° C.

Ethoxy-1,1,1-trifluoro-3-buten-2-one was obtained in an isolated yield of 87% of the theoretical yield and with a purity (cis+trans isomer) of 98%.

EXAMPLE 3

Conversion of CETFBO to ETFBO by Thermolysis Treatment

General procedure: After the reaction of step (a), as described above in example 1, the flask, fitted with a reflux condenser, was heated to the desired temperature by using an oil bath. The thermolysis or flash thermolysis was performed under different conditions: at different temperatures, with or without an inert gas stream or under vacuum. The conversion of CETFBO to ETFBO was followed by GC analyses. When the composition of the reaction mixture remained constant, the resulting reaction mixture was further subjected to a distillation in vacuo (70° C., 20 mbar) to obtain Ethoxy-1,1,1-trifluoro-3-buten-2-one. The experimental data are summarized in Table 1. The thermolysis time refers to the time after which the composition of the reaction mixture remained constant.

TABLE 1

| Example | Conditions | Thermolyis time [min] | % wt of CETFBO | % wt of ETFBO (cis/trans) | Isolated yield of ETFBO (%) |
|---|---|---|---|---|---|
| 3a | 80° C. | 43 | 5.2 | 88.9/1.3 | 85.7 |
| 3b | 80° C./N$_2$ stream (24 l/h) | 80 | 0.3 | 97.6/1.6 | 91.5 |
| 3c | 80° C./ vacuum (400 mbar) | 80 | 1.4 | 95.1/1.7 | 89.3 |
| 3d | 120° C. | 17 | 1.2 | 94.3/1.4 | 89.9 |
| 3e | flash thermolysis 120° C. | 13 | 1.0 | 94.9/1.5 | 93.0 |
| 3f | flash thermolysis 100° C. | 25 | 2.8 | 93.7/1.4 | 93.7 |

The % wt of CETFBO and % wt of ETFBO (cis/trans) were measured by GC analyses.

The % wt of CETFBO and %wt of ETFBO (cis/trans) were measured by GC analyses.

The invention claimed is:

1. A process for preparing an alkenone, which comprises the following steps:
   (a) providing a halogenated precursor of the alkenone, wherein the halogenated precursor of the alkenone corresponding to Formula (I): R1-C(O)—CH2-CH(X)—OR2 (I) wherein X represents fluorine, chlorine or bromine; wherein R1 is a fluorinated C1-C4 alkyl group or R1 represents CF3C(O)CH2; and wherein R2 represents aryl, substituted aryl, or a C1-C10 alkyl group which is optionally substituted by at least one halogen atom is prepared by reaction of an acid halide corresponding to Formula (II): R1-C(O)X (II) in which X and R1 has the same meaning as in Formula (I), is reacted with a vinyl ether corresponding to Formula (III): CH2=C(H)—OR2 (III) in which R2 has the same meaning as in Formula (I); and
   (b) eliminating the hydrogen halide from said precursor to form the alkenone by a thermolysis treatment selected from the group consisting of a thermolysis carried out at a temperature from greater than 90° C. to 120° C., a flash thermolysis, vacuum thermolysis carried out at a temperature from 60° C. to 140° C., and thermolysis under stripping with inert gas.

2. The process according to claim 1, wherein R2 is a C1-C4 alkyl group.

3. The process according to claim 1, wherein the carboxylic acid halide is trifluoroacetyl chloride.

4. The process according to claim 1, wherein the thermolysis is selected from the group consisting of flash thermolysis and thermolysis under stripping with inert gas, and is carried out at a temperature of from −20° C. to 140° C.

5. The process according to claim 1, wherein said thermolysis is carried out under a gas stream.

6. The process according to claim 1, wherein said thermolysis is carried out under stripping with nitrogen.

7. The process according to claim 1, wherein said thermolysis is carried out under vacuum.

8. The process according to claim 7, wherein said thermolysis is carried out under a vacuum of from 100 to 600 mbar.

9. The process according to claim 1, wherein said thermolysis is a flash thermolysis with a heating time of less than 1 hour.

10. The process according to claim 9, wherein the thermolysis is carried out for a period of time ranging from 30 seconds to less than 1 hour.

11. The process according to claim 1, which is carried out batchwise.

12. The process according to claim 1, which is carried out continuously.

13. The process according to claim 1, which further comprises separating the alkenone ether produced in step (b) from hydrogen halide, unreacted carboxylic acid halide and unreacted halogenated precursor and optionally recycling carboxylic acid halide to step (a) and halogenated precursor to step (b).

14. The process according to claim 1, wherein R1 is a methyl, ethyl group, n-propyl or isopropyl group substituted by at least one fluorine atom.

15. The process according to claim 1, wherein R1 is CF3.

16. The process according to claim 9, wherein the flash thermolysis is conducted at a temperature ranging from 0° C. to 130° C. and for a period of time ranging from 30 seconds to 30 minutes.

17. The process according to claim 9, wherein the flash thermolysis is conducted at a temperature ranging from 50° C. to 120° C. and for a period of time ranging from 30 seconds to 20 minutes.

18. The process according to claim 9, wherein the flash thermolysis is carried out under stripping with an inert gas stream.

19. The process according to claim 9, wherein the flash thermolysis is carried out under vacuum.

* * * * *

UNITED STATES PATENT AND TRADEMARK OFFICE
CERTIFICATE OF CORRECTION

PATENT NO. : 8,440,865 B2
APPLICATION NO. : 12/999750
DATED : May 14, 2013
INVENTOR(S) : Max Braun et al.

Page 1 of 1

It is certified that error appears in the above-identified patent and that said Letters Patent is hereby corrected as shown below:

IN THE SPECIFICATION:

on column 2, line 12:
"Formula (I): R1-C(O)-C(H)=C(H)-OR2 (I)" should read
"Formula (IV): R1-C(O)-C(H)=C(H)-OR2 (IV)".

on column 2, line 50:
"halogenated precursor of the alkenone" should be followed by
"corresponding to Formula (I): R1-C(O)-CH2-CH(X)-OR2 (I)".

Signed and Sealed this
Eighth Day of October, 2013

Teresa Stanek Rea
*Deputy Director of the United States Patent and Trademark Office*